United States Patent
Ito et al.

(10) Patent No.: US 11,710,423 B2
(45) Date of Patent: Jul. 25, 2023

(54) ENDOSCOPE MANIPULATION TRAINING APPARATUS

(71) Applicant: Wine Red Co., Ltd., Tokyo (JP)

(72) Inventors: Yoshiaki Ito, Tokyo (JP); Yasuhisa Abe, Kanagawa (JP)

(73) Assignee: Wine Red Co., Ltd., Tokyo (JP)

( * ) Notice: Subject to any disclaimer, the term of this patent is extended or adjusted under 35 U.S.C. 154(b) by 951 days.

(21) Appl. No.: 16/513,245

(22) Filed: Jul. 16, 2019

(65) Prior Publication Data
US 2020/0027373 A1    Jan. 23, 2020

(30) Foreign Application Priority Data
Jul. 17, 2018    (JP) ................................ 2018-133799

(51) Int. Cl.
*G09B 23/28* (2006.01)
*A61B 1/00* (2006.01)

(52) U.S. Cl.
CPC ........ *G09B 23/285* (2013.01); *A61B 1/00154* (2013.01)

(58) Field of Classification Search
USPC ........................................................ 434/272
See application file for complete search history.

(56) References Cited

U.S. PATENT DOCUMENTS

2001/0016804 A1* 8/2001 Cunningham ....... G09B 23/285
                                                                  703/7
2012/0308977 A1* 12/2012 Tortola ................. G09B 23/285
                                                                434/262

FOREIGN PATENT DOCUMENTS

| JP | 4502757   | B2 | * | 7/2010  |
| JP | 3177527   | U  | * | 8/2012  |
| JP | 2016218415 | A  | * | 12/2016 |

* cited by examiner

*Primary Examiner* — Jay Trent Liddle
*Assistant Examiner* — Alyssa N Brandley
(74) *Attorney, Agent, or Firm* — Socal IP Law Group LLP; Brian Tamsut (57) ABSTRACT

An endoscope manipulation training apparatus includes: a body including an organ support plate, two support leg plates, and an insertion tube support body; and a net body. Fitting portions are formed on both end portions of the organ support plate, threaded holes are formed in both corner portions of both end surfaces of the organ support plate, a fitting hole is formed in one of the fitting portions such that the fitting hole extends inward from an end surface of the fitting portion, and a latch groove is formed in the one of the fitting portions on both sides of the fitting hole. The support leg plate is formed such that an inner peripheral surface and an outer peripheral surface exhibit a regular octagonal shape.

4 Claims, 14 Drawing Sheets

ENDOSCOPE MANIPULATION TRAINING APPARATUS

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This patent claims priority from Japanese patent application number JP2018-133799, filed Jul. 17, 2018, with the title: ENDOSCOPE MANIPULATION TRAINING APPARATUS, of which are incorporated herein by reference in their entirety.

BACKGROUND

Field

This disclosure relates to an endoscope manipulation training apparatus suitable for training a manipulation in inspecting the inside of a human body, particularly, the inside of a digestive system tubular organ such as an esophagus, a stomach, a small intestine or a large intestine using an endoscope and in performing an operation.

Description of the Related Art

Recently, in inspecting the inside of a human body, a method has been adopted where a distal end portion of an endoscope is inserted into the human body from a mouth or an anus, and the inside of a digestive organ is directly observed. By adopting such a method, the inside of a human body can be inspected easily, speedily, and accurately. Further, it is also possible to perform an operation of removing a polyp generated in an organ or the like simultaneously with the inspection.

However, in the course of the inspection where the distal end portion of the endoscope is inserted into and moved in an organ, there is a concern that an inner wall surface of the organ is damaged by the distal end portion of the endoscope. Further, it is necessary for a person who performs an operation of removing a polyp or the like to sufficiently learn a manipulation of an endoscope.

Under such circumstances, before the inside of a human body is actually inspected and an operation is performed by manipulating the endoscope, a training of a manipulation of an endoscope is performed using a sampled organ. There have been developed various types of endoscope manipulation training apparatus for assisting such training (see JP 2006-81568 A, Utility Model Registration No. 3162161, and Utility Model Registration No. 3177527).

In an endoscope manipulation training apparatus disclosed in JP 2006-81568 A, an opening portion 14 is formed in a center portion of a support base 10, a cylindrical body 1 to which one end portion of a tubular organ is connected and a rod-like body 2 to which the other end portion of the tubular organ is connected are disposed, both end portions of the tubular organ are connected to the cylindrical body 1 and the rod-like body 2, and a center portion of the tubular organ is positioned in the opening portion 14.

In an endoscope manipulation training apparatus disclosed in Utility Model Registration No. 3162161, an opening portion is formed in a center portion of a ceiling plate portion 1 of an apparatus body, two net bodies 16, 17 having flexibility are disposed in the opening portion, a tubular organ is placed on the net bodies 16, 17, and a portion of the organ is disposed so as to pass through meshes of the net bodies 16, 17.

In an endoscope manipulation training apparatus disclosed in Utility Model Registration No. 3177527, an opening portion is formed in a center portion of the apparatus body 1, leg portions 2, 2 each having a polygonal shape are disposed on both end portions of the apparatus body 1, a tubular organ is placed on net bodies 14, 15 disposed in the opening portion, and a set angle of the tubular organ can be changed by rotating the leg portions 2, 2 to a suitable angle.

With respect to the endoscope manipulation training apparatus disclosed in JP 2006-81568 A, there may be a case where the position and the posture of the tubular organ when the tubular organ is disposed on the manipulation training apparatus and the position and the posture of the tubular organ when the tubular organ is actually disposed in a human body largely differ from each other. That is, the actual tubular organ is disposed not only in a straight line shape but also in a state where the tubular organ is bent upward, downward, leftward, or rightward. Accordingly, the endoscope manipulation training apparatus disclosed in JP 2006-81568 A has a drawback that the position and the posture of the tubular organ cannot be accurately reproduced.

In the endoscope manipulation training apparatus disclosed in Utility Model Registration No. 3162161, the tubular organ is placed on the net bodies 16, 17, and a portion of the organ is disposed so as to pass through the meshes of the net bodies 16, 17. Accordingly, the tubular organ can be disposed not only in a straight line shape but also in a state where the tubular organ is bent upward, downward, leftward, or rightward in the same manner as an actual tubular organ disposed in a human body and hence, it is possible to approximately accurately reproduce the position and the posture of the actual tubular organ.

However, during the use of an endoscope or during the manipulation of the endoscope, for the purpose of more safely and properly performing an inspection or an operation, it is necessary to set a body position of a patient in a posture where the patient is rotated by a predetermined angle. However, in the endoscope manipulation training apparatus disclosed in Utility Model Registration No. 3162161, the position and the posture of a tubular organ cannot be rotated by a predetermined angle. Accordingly, with respect to the position and the posture of the actual tubular organ disposed in a human body, training of a manipulation of an endoscope for inspection and operation cannot be performed.

On the other hand, in the endoscope manipulation training apparatus disclosed in Utility Model Registration No. 3177527, the leg portions 2, 2 having a polygonal shape are disposed on both end portions of the apparatus body 1, and a set angle of a tubular organ can be changed by rotating the leg portions 2, 2 at a suitable angle. Accordingly, training of a manipulation of an endoscope for inspection and operation can be performed in a state similar to the position and the posture of an actual tubular organ disposed in a human body by rotating the leg portions 2, 2 at a predetermined angle.

However, in the endoscope manipulation training apparatus disclosed in Utility Model Registration No. 3177527, in performing endoscope manipulation training with respect to many types of tubular organs, assembling, disassembling and the like of the apparatus cannot be performed easily, setting and exchanging of a tubular organ also take time, and cleaning or the like of the apparatus cannot be performed easily.

The leg portions 2, 2 have a polygonal shape and hence, in performing endoscope manipulation training, the apparatus is liable to be rotated thus giving rise to a drawback with respect to stability.

Further, when a tubular organ is used in a state where the tubular organ is immersed in physiological saline, a container in which physiological saline is stored is liable to move thus giving rise to a drawback with respect to stability.

SUMMARY OF THE INVENTION

The present invention has been made in view of the above-mentioned drawbacks, and it is an object of the present invention to provide an endoscope manipulation training apparatus where assembling, disassembling and the like of the apparatus can be performed easily, setting and exchanging of a tubular organ do not take time, and the apparatus is minimally rotated when endoscope manipulation training is performed, and electrified bath in which physiological saline is stored is minimally moved thus providing excellent stability to the endoscope manipulation training apparatus.

To achieve the above-mentioned object, an endoscope manipulation training apparatus according to the present invention includes: a body including an organ support plate, two support leg plates, and an insertion tube support body; and a synthetic-resin-made net body having flexibility, wherein an opening portion is formed in a center portion of the organ support plate, fitting portions are formed on both end portions of the organ support plate, threaded holes are formed in both corner portions of both end surfaces of the organ support plate, a fitting hole is formed in one of the fitting portions such that the fitting hole extends inward from an end surface of the fitting portion, and a latch groove is formed in the one of the fitting portions on both sides of the fitting hole, the support leg plate is formed such that an outer peripheral surface and an inner peripheral surface exhibit a regular octagonal shape, a cutaway portion is formed in an upper end portion of the support leg plate, fitting portions are formed in center portions of the inner peripheral surface of the support leg plate, and the insertion holes are formed in the support leg plate on outer sides with respect to the fitting grooves, and the insertion tube support body includes a protruding portion, a holding portion, and a fitting engagement groove, and the protruding portion is fitted into the fitting hole of the organ support plate.

In such a configuration, the body further includes an electrified bath support plate, and an opening portion is formed in a center portion of the electrified bath support plate, and placing portions are formed on both end portions of the electrified bath support plate.

The endoscope manipulation training apparatus according to the present invention further includes a base, wherein the base includes a rectangular base plate, and pedestal bodies disposed on four corner portions of the base plate.

According to the endoscope manipulation training apparatus of the present invention, assembling, disassembling and the like of the apparatus can be performed easily and hence, mounting and exchanging of a tubular organ do not take time, and cleaning or the like of the apparatus can be performed easily.

Further, in performing endoscope manipulation training, the apparatus is minimally rotated and the electrified bath in which physiological saline is stored is minimally moved. Accordingly, the endoscope manipulation training apparatus of the present invention exhibits excellent stability.

DESCRIPTION OF THE DRAWINGS

FIGS. 7A to 7C are views showing a base of the endoscope manipulation training apparatus according to the present invention, where

FIGS. 9A and 9B are views showing a support leg plate of the endoscope manipulation training apparatus according to the present invention, wherein

FIGS. 10A to 10D are views showing an insertion tube support body of the endoscope manipulation training apparatus according to the present invention, wherein

FIGS. 13A to 13C are views showing a pedestal body of the endoscope manipulation training apparatus according to the present invention, wherein

DETAILED DESCRIPTION

Description of Apparatus

Hereinafter, a preferred embodiment of an endoscope manipulation training apparatus according to the present invention is described in detail with reference to drawings.

As shown in FIG. 1 to FIG. 17, the endoscope manipulation training apparatus 1 according to the present invention includes a body 2, a net body 3, a base 4, an insertion tube 5, and an electrified bath 6.

As shown in FIG. 1 to FIG. 6, the body 2 includes an organ support plate 11, support leg plates 12, 12, an insertion tube support body 13, and an electrified bath support plate 14.

Figure 8:
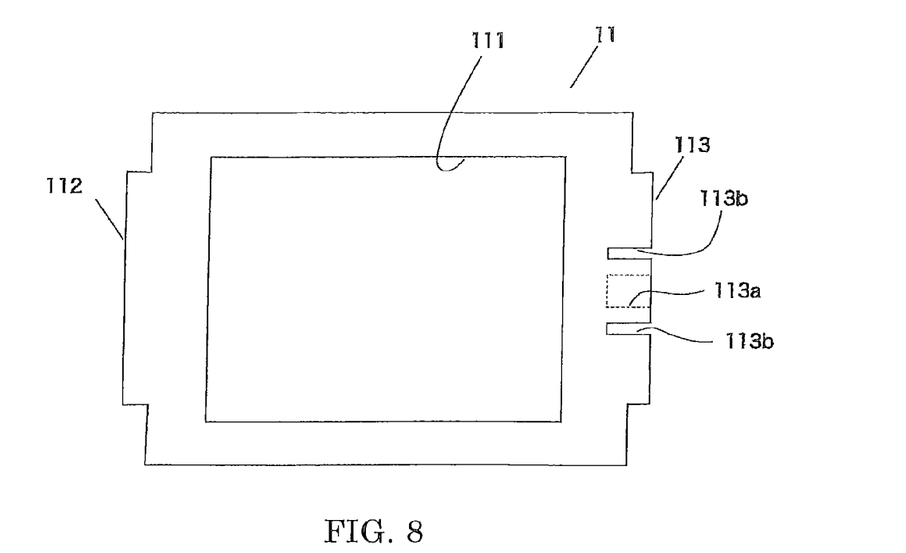
FIG. 8 is a plan view showing an organ support plate of the endoscope manipulation training apparatus according to the present invention.

As shown in FIG. 8, an opening portion 111 having a large area is formed in a center portion of the organ support plate 11, and fitting portions 112, 113 are formed on both end portions of the organ support plate 11.

Threaded holes 11a, 11a are formed in both corner portions of both end surfaces of the organ support plate 11.

A fitting hole 113a is formed in an end surface of a center portion of the fitting portion 113 on a right side. The fitting hole 113a extends into the organ support plate 11 from the end surface. Latch grooves 113b, 113b are formed in the end surface on both sides of the fitting hole 113a.

A plurality of hooks 114, 114, ... are disposed on an upper surface of the organ support plate 11 around the opening portion 111, and a stop ring 115 is disposed on the upper surface of the organ support plate 11 on a left side of the opening portion 111.

Figure 9A:
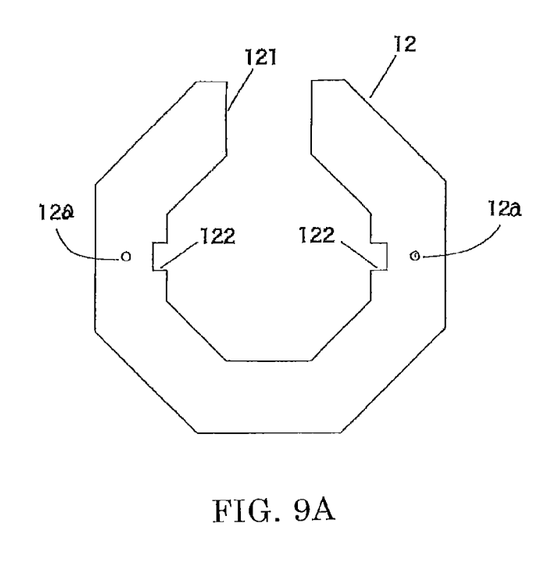
FIG. 9A is a front view and FIG. 9B is a side view.
Figure 9B:
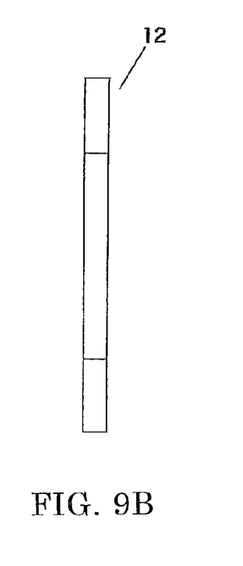
Figure 10A:
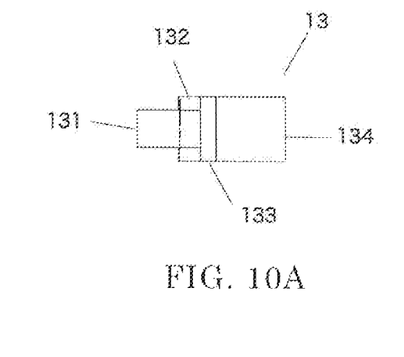
FIG. 10A is a plan view.
Figure 10B:
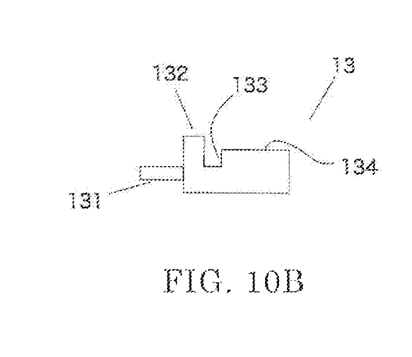
FIG. 10B is a front view.
Figure 10C:
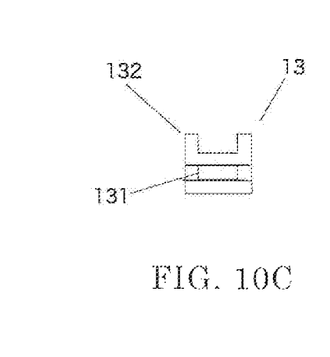
FIG. 10C is a left side view.
Figure 10D:
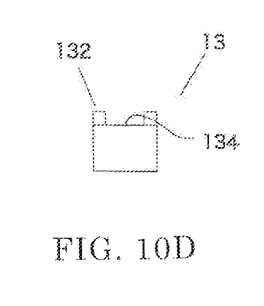
FIG. 10D is a right side view.

As shown in FIG. 9A, the support leg plate 12 is formed such that an outer peripheral surface and an inner peripheral surface exhibit a regular octagonal shape. A cutaway portion 121 is formed in an upper end portion of the support leg plate 12.

Fitting grooves 122 are formed in center portions of an inner peripheral surface, and insertion holes 12a are formed in the support leg plate 12 on outer sides with respect to the fitting grooves 122.

As shown in FIGS. 10A to 10D, the insertion tube support body 13 includes a protruding portion 131, a holding portion 132, a fitting engagement groove 133, and a flat portion 134.

The protruding portion 131 is formed such that the protruding portion 131 is fitted into the fitting hole 113a of the organ support plate 11.

Figure 11:
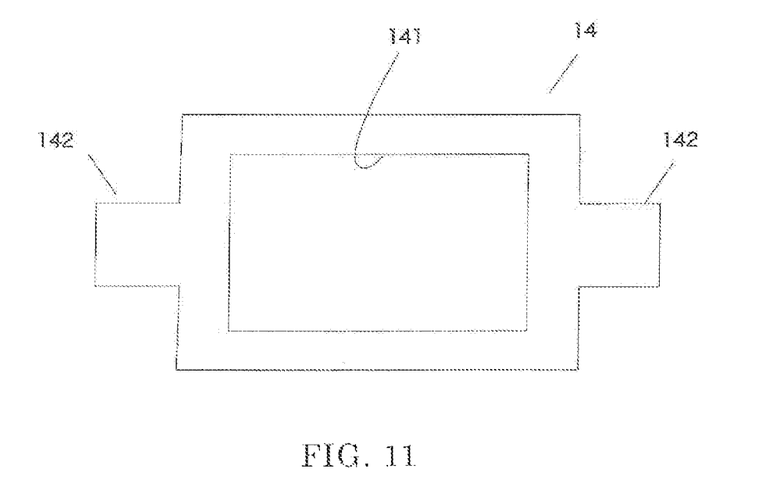
FIG. 11 is a plan view of an electrified bath support plate of the endoscope manipulation training apparatus according to the present invention.
Figure 12:
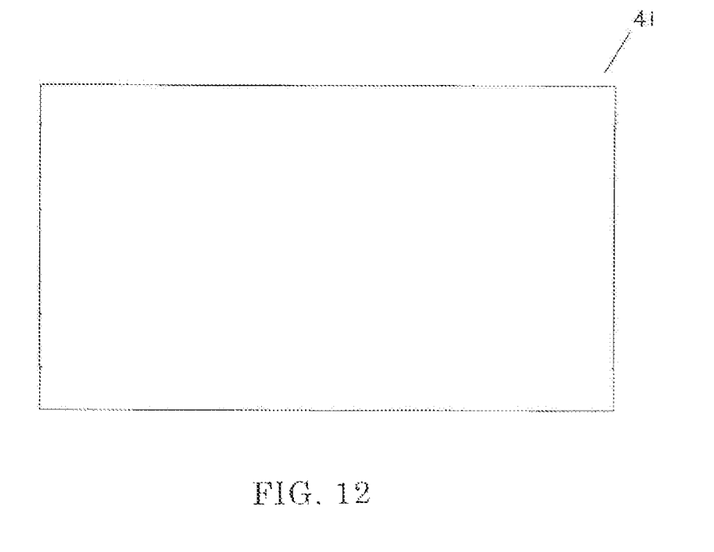
FIG. 12 is a plan view of a base plate of the endoscope manipulation training apparatus according to the present invention.

As shown in FIG. 11, an opening portion 141 having a large area is formed in a center portion of the electrified bath support plate 14, and placing portions 142 are formed on both end portions of the electrified bath support plate 14.

The electrified bath 6 for storing physiological saline in which a tubular organ is immersed is disposed in the opening portion 141.

Figure 14:
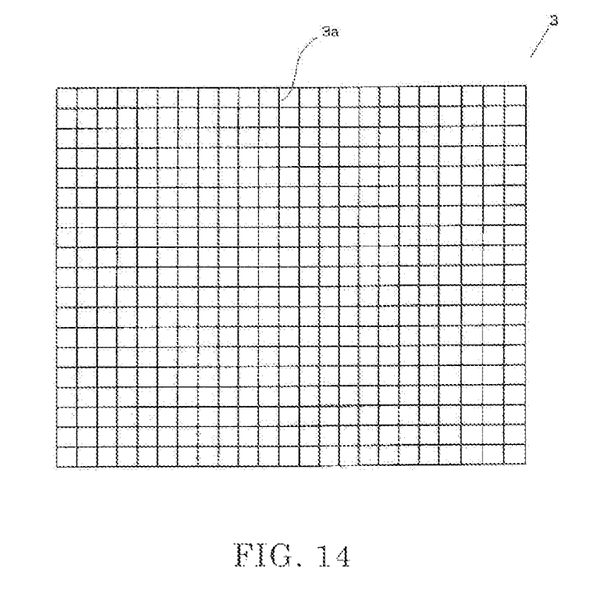
FIG. 14 is a front view of a net body of the endoscope manipulation training apparatus according to the present invention.

As shown in FIG. 14, the net body 3 is a synthetic-resin-made grid-like net body having flexibility. Two net bodies 3 may be used in a vertically overlapping manner.

As shown in FIGS. 7A to 7C, FIG. 12, and FIGS. 13A to 13C, the base 4 includes a base plate 41 having a rectangular shape, and pedestal bodies 42, 42 ... disposed at four corner portions of the base plate 41.

Figure 13A:
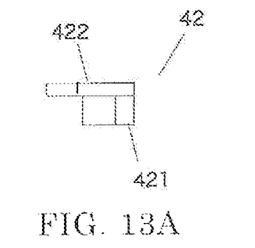
FIG. 13A is a plan view.
Figure 13B:
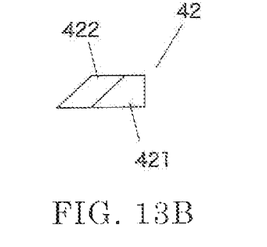
FIG. 13B is a front view.
Figure 13C:
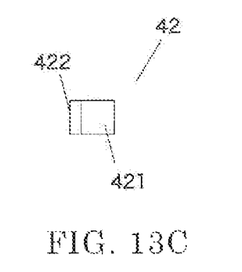
FIG. 13C is a left side view.

The pedestal body 42 includes a holding portion 421 disposed on an inner side and a restricting portion 422 disposed on an outer side. An inner-side inclined surface of the holding portion 421 is formed with an inclination angle of approximately 45°.

Figure 15:
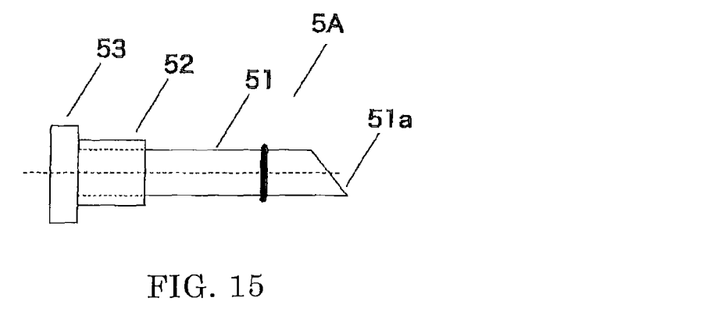
FIG. 15 is a front view of an insertion tube of the endoscope manipulation training apparatus according to the present invention.
Figure 16:
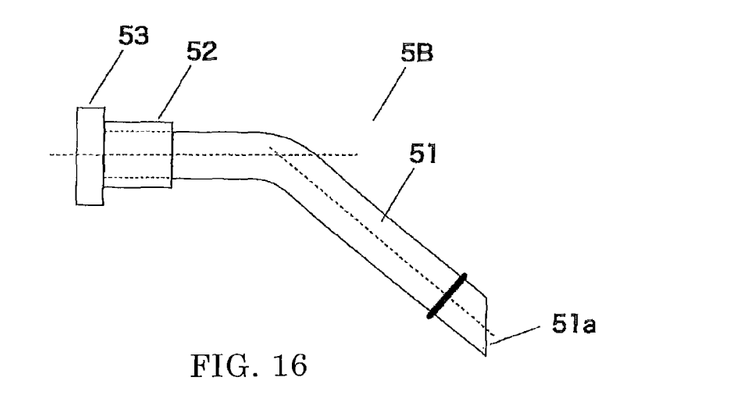
FIG. 16 is a front view of an insertion tube of the endoscope manipulation training apparatus according to the present invention.

As shown in FIG. 15 and FIG. 16, the insertion tube 5a and 5b, respectively, includes a tubular portion 51, a grip portion 52, and an adaptor portion 53.

A distal end portion 51a of the tubular portion 51 is fitted into one end opening portion of a tubular organ, a distal end portion of an endoscope FS (see FIG. 19) is inserted from the adaptor portion 53, and the distal end portion of the endoscope FS is introduced into the tubular organ.

Figure 17:
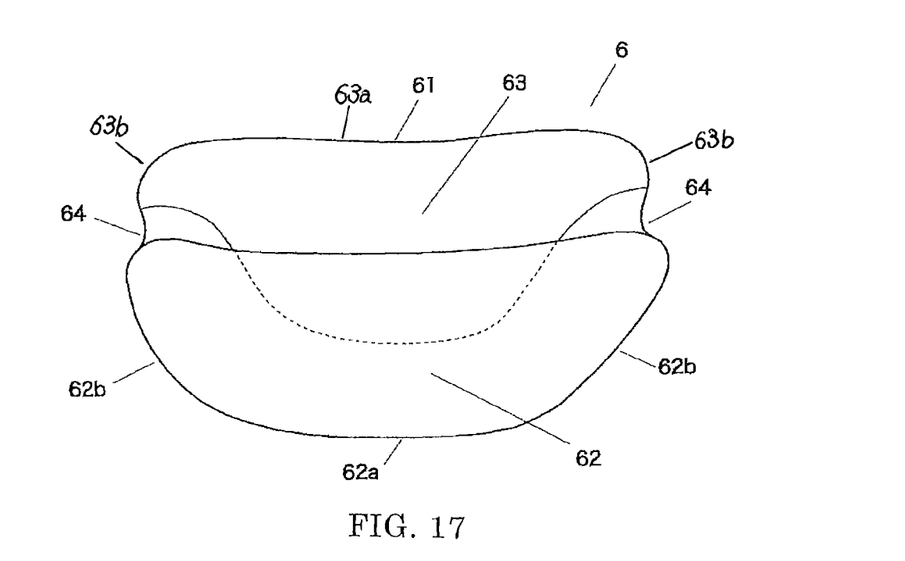
FIG. 17 is a perspective view of an electrified bath according to the present invention.

As shown in FIG. 17, the electrified bath 6 is a bag-shaped bath having an opening 61 on an upper end thereof. The electrified bath 6 is formed by molding a thin metal sheet having electric conductivity. As the metal sheet having electric conductivity, a copper sheet is particularly preferably used.

With respect to a front portion 62 and a back portion 63, a width of both end portions 62b, 63b is set slightly narrower than a width of intermediate portions 62a, 63a, and the opening 61 at both side portions 64 is positioned lower than the opening 61 at the front portion 62 and the back portion 63.

Next, an assembling method and a using method of the body 2 of the endoscope manipulation training apparatus 1 according to the present invention are described in detail.

Figure 2:
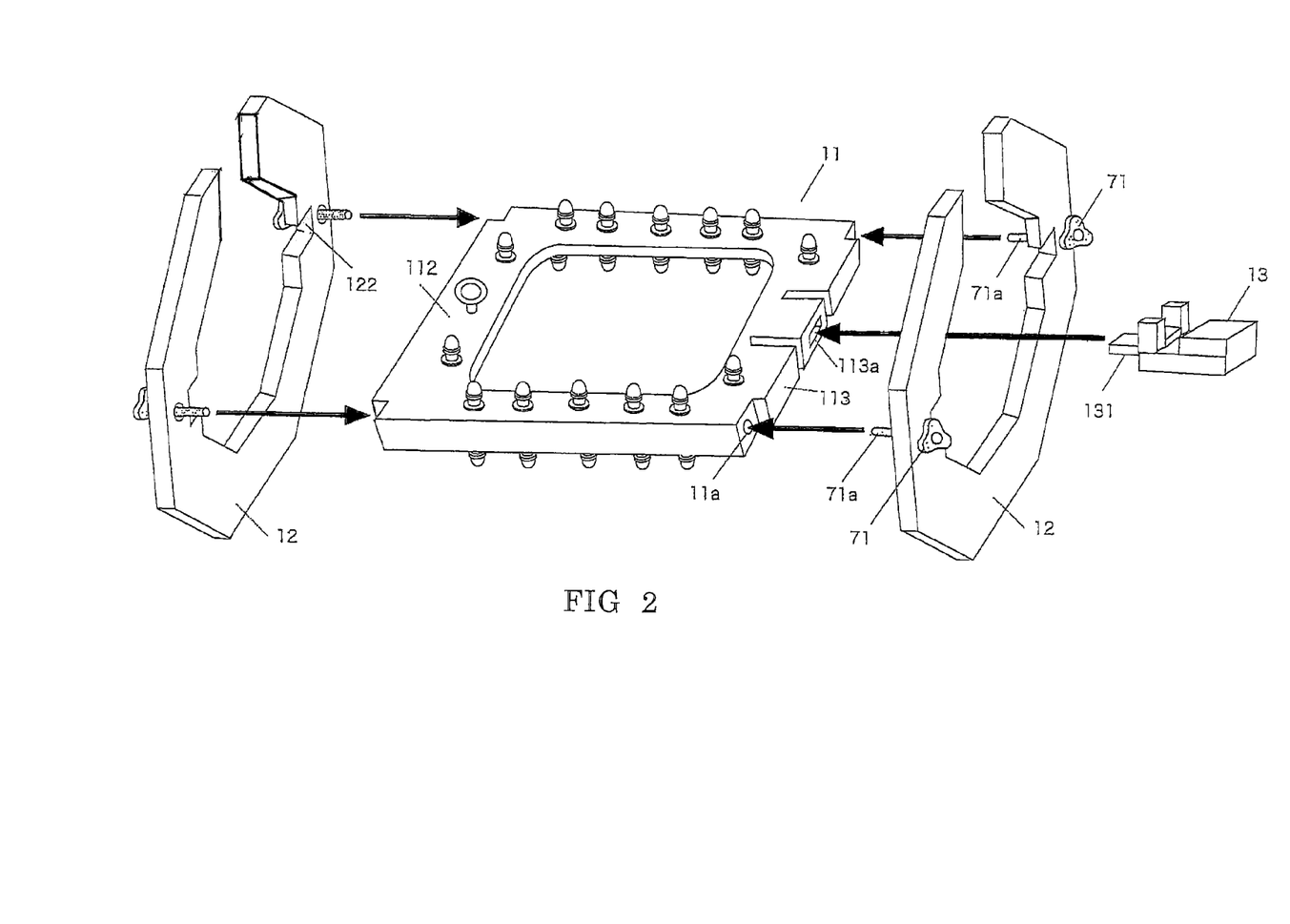
FIG. 2 is an exploded perspective view of the body of the endoscope manipulation training apparatus according to the present invention.
Figure 3:
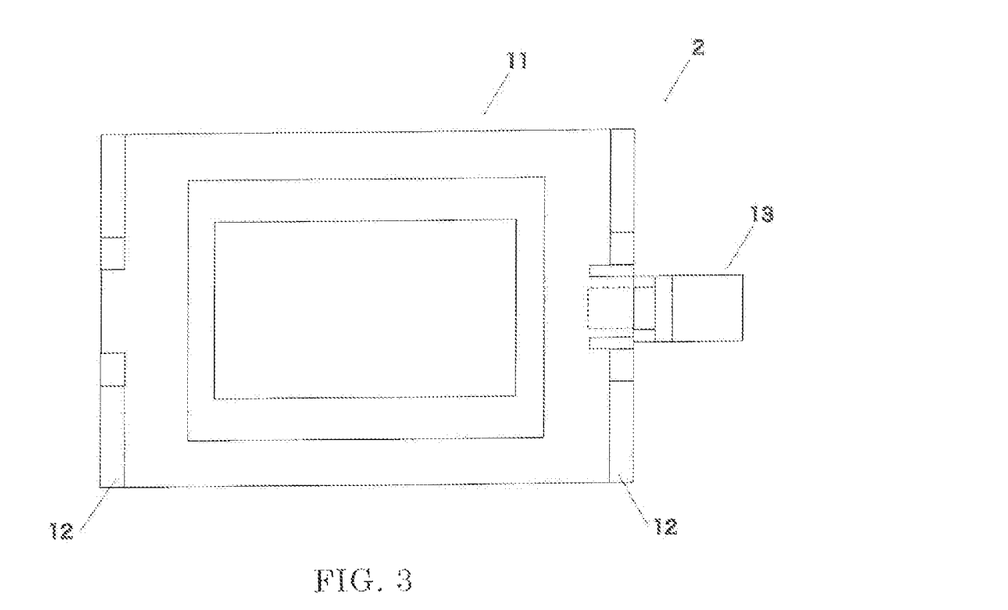
FIG. 3 is a plan view of the body of the endoscope manipulation training apparatus according to the present invention.
Figure 4:
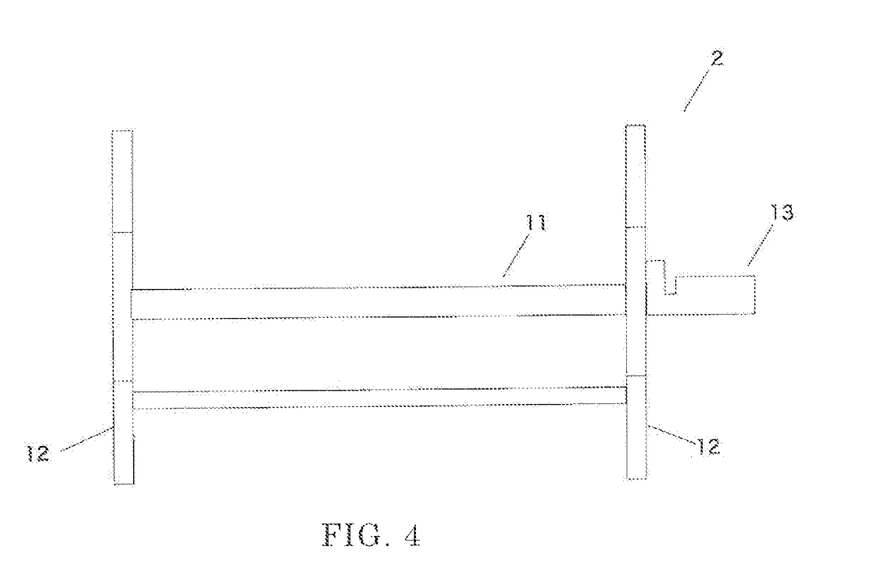
FIG. 4 is a front view of the body of the endoscope manipulation training apparatus according to the present invention.
Figure 5:
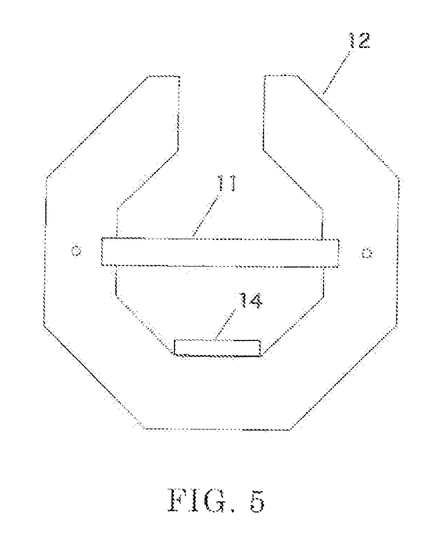
FIG. 5 is a left side view of the body of the endoscope manipulation training apparatus according to the present invention.
Figure 6:
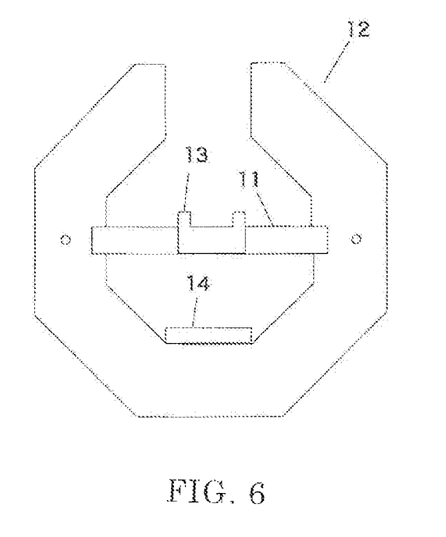
FIG. 6 is a right side view of the body of the endo scope manipulation training apparatus according to the present invention.
Figure 7A:
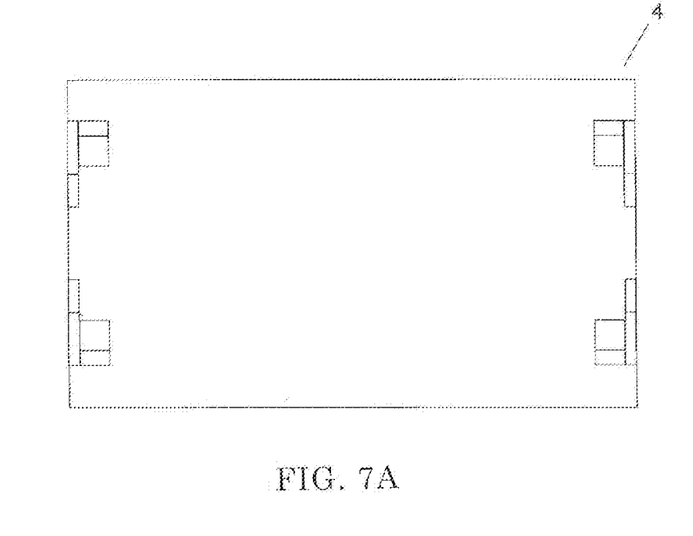
FIG. 7A is a plan view.
Figure 7B:
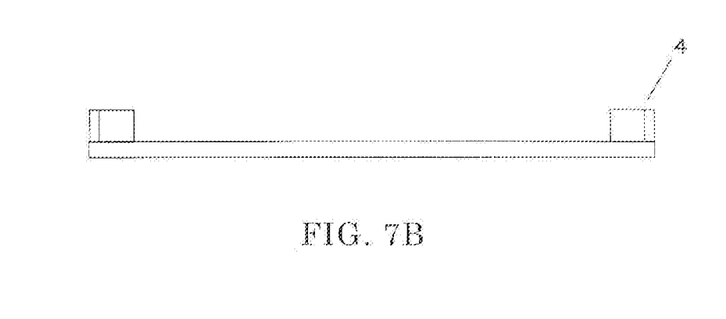
FIG. 7B is a front view.
Figure 7C:
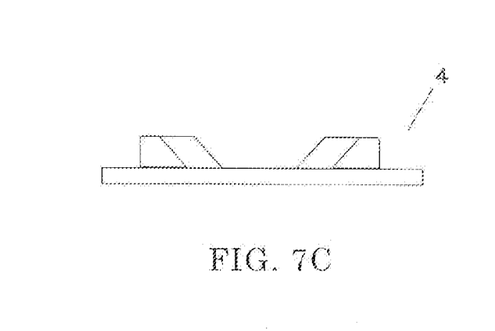
FIG. 7C is a right side view.

Firstly, as shown in FIG. 2, two support leg plates 12, 12 are made to approach the organ support plate 11 from both sides of the organ support plate 11. The fitting portions 112, 113 formed on both end portions of the organ support plate 11 are made to engage with the fitting grooves 122, 122 of the respective support leg plates 12, 12 by fitting engagement.

Then, threaded portions 71a of butterfly screws 71 are made to pass through the insertion holes 120 of the support leg plates 12 and are threadedly engaged with the threaded holes 11a formed in the organ support plate 11 thus connecting the support leg plates 12, 12 to both side portions of the organ support plate 11.

Figure 1:
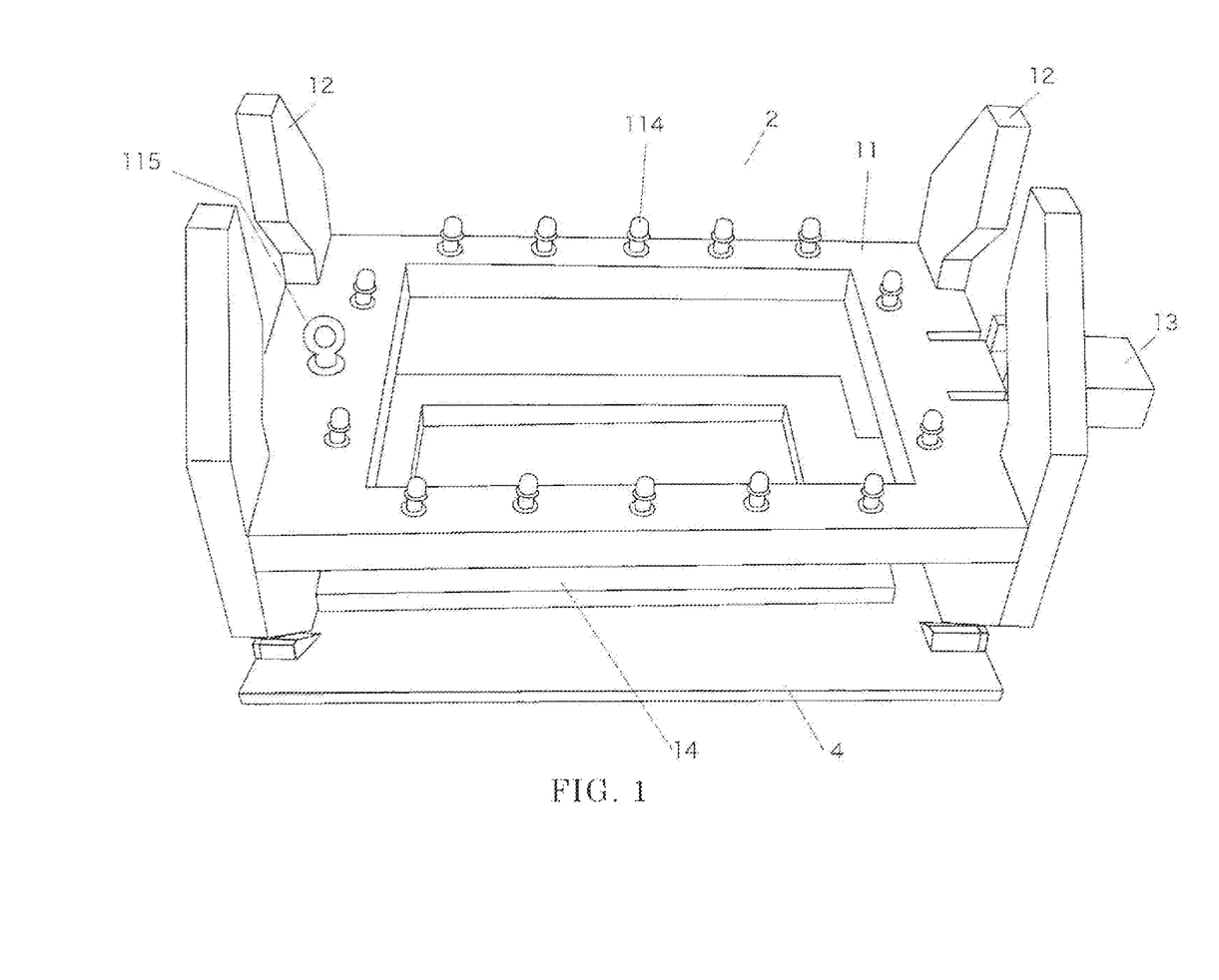
FIG. 1 is a perspective view of a body of an endoscope manipulation training apparatus according to the present invention.

Next, as shown in FIG. 2, the protruding portion 131 of the insertion tube support body 13 is fitted into the fitting hole 113a formed in the end surface of the organ support plate 11 on a right side. As a result, as shown in FIG. 1, the body 2 of the endoscope manipulation training apparatus 1 in a state where the electrified bath support plate 14 is not mounted can be assembled.

Then, as shown in FIG. 3 to FIG. 6, the placing portions 142, 142 formed on both end portions of the electrified bath support plate 14 are placed on bottom surfaces of inner peripheries of two support leg plates 12, 12 thus assembling the body 2 of the endoscope manipulation training apparatus 1 in a state where the electrified bath support plate 14 is mounted.

On the other hand, by carrying out steps opposite to the above-mentioned assembling steps, the body 2 of the endoscope manipulation training apparatus 1 can be easily disassembled into the organ support plate 11, support leg plates 12, 12, and the electrified bath support plate 14.

As has been described above, according to the endoscope manipulation training apparatus 1 of the present invention, assembling, disassembling and the like of the apparatus can be performed easily and hence, mounting and exchanging of an tubular organ do not take time, and cleaning or the like of the apparatus can be performed easily.

As shown in FIG. 1, bottom surfaces of outer peripheries of the support leg plates 12, 12 are placed on the upper surface of the base plate 41 of the base 4 and inclined surfaces of the outer peripheries of the support leg plates 12, 12 are brought into contact with inclined surfaces of the pedestal bodies 42, 42, . . . . Accordingly, the body 2 of the endoscope manipulation training apparatus 1 can be held by the base 4 in a stable manner.

Accordingly, in performing endoscope manipulation training, the apparatus is minimally rotated and the electrified bath 6 in which physiological saline is stored is minimally moved. Accordingly, the endoscope manipulation training apparatus 1 of the present invention exhibits excellent stability.

Next, the description is made with respect to the case where an endoscope manipulation training is performed with an esophagus ES adopted as a training object by using the endoscope manipulation training apparatus 1 according to the present invention.

Firstly, in a state where the body 2 of the endoscope manipulation training apparatus 1 is stably held by the base 4, the net body 3 is placed on the opening portion 111 formed in the center portion of the organ support plate 11 such that the net body 3 covers the opening portion 111. Then, the hooks 114 are made to pass through and are latched to meshes 3a of the net body 3 so that the net body 3 is set in a suitable state.

Next, the distal end portion 51a of the tubular portion 51 of the insertion tube 5 is fitted into the opening portion formed in one end of the esophagus ES, the grip portion 52 is positioned on the holding portion 132 of the insertion tube support body 13, and the adaptor portion 53 is fitted in the fitting engagement groove 133 of the insertion tube support body 13.

Then, a face fastener 72 is made to pass through the latch grooves 113b, 113b formed in the organ support plate 11, a proximal end portion 51b of the tubular portion 51 of the insertion tube 5 is wound by the face fastener 72 so that the proximal end portion 51b is fastened. Accordingly, the insertion tube 5 can be supported on the insertion tube support body 13.

Next, the opening portion of the esophagus ES on the other end is sutured by a suture thread 73, and the other end portion of the suture thread 73 is tied to the stop ring 115. Accordingly, the esophagus ES can be set and held on the net body 3 in a predetermined state.

The cutaway portion 121 is formed in the upper end portion of the support leg plate 12 and hence, the esophagus ES where the distal end portion 51a of the insertion tube 5 is fitted into the opening portion at one end thereof can be placed on the net body 3 through the cutaway portion 121. Accordingly, an operation of setting and holding the esophagus ES can be facilitated.

As has been described above, in a state where the esophagus ES is set and held on the net body 3 in a predetermined state, the distal end portion of the endoscope FS (see FIG. 19) is inserted from the adaptor portion 53 of the insertion tube 5, and the distal end portion of the endoscope FS is moved in the esophagus ES. With such an operation, training of inspection and operation of an inner wall surface of the esophagus ES using the endoscope FS can be performed in a state similar to an actual inspection and operation.

Further, according to the endoscope manipulation training apparatus 1 of the present invention, an endoscope manipulation training can be also performed with a tubular organ such as a large intestine LI cut away from a living body and is bent upward, downward, leftward, or rightward adopted as a training object.

Figure 20:
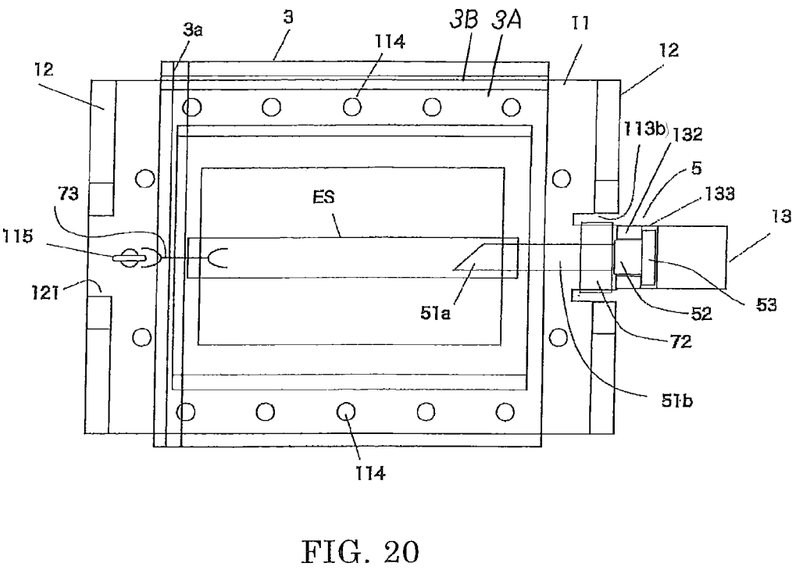
FIG. 20 is a plan view showing a use state of the endoscope manipulation training apparatus according to the present invention.

When the large intestine LI is adopted as an training object, firstly, in a state where the body 2 of the endoscope manipulation training apparatus 1 is held on the base 4 in a stable manner, two net bodies 3A, 3B are placed on the opening portion 111 formed in the center portion of the organ support plate 11 in a vertically covering manner, and the net body 3B on a lower side is stretched such that the net body 3B is formed in a downward U shape.

The distal end portion 51a of the insertion tube 5 is fitted into an intestine rectum LI1 of the large intestine LI, and the intestine rectum LI1 is tied and set to the net body 3B on a lower side. Then, a suitable portion of the large intestine LI is inserted into and is made to pass through a cut hole of the net body 3A on an upper side, and is exposed above the net body 3A on an upper side while forming a sigmoid colon LI2.

Then, the suitable portion of the large intestine LI is inserted into and is made to pass through a cut hole of the net body 3A on an upper side, is placed on the net body 3B on a lower side. Thereafter, again, the suitable portion of the large intestine LI is placed on the net body 3A on an upper side through a cut hole of the net body 3A on an upper side thus forming a flexura coli sinistra LI3. Then, a colon transversum LI4 is formed.

Then, the suitable portion of the large intestine LI is inserted into and is made to pass through a cut hole of the net body 3A on an upper side, is placed on the net body 3B on a lower side, a flexura coli dextra LI5 is formed, and blind gut LI6 is formed. Accordingly, the large intestine LI can be set with a configuration and a posture of an actual large intestine LI.

During endoscope manipulation training, along with a lapse of a training time, moisture of a tubular organ is dissipated due to natural vaporization. Accordingly, electric conductivity of an electric knife of the endoscope FS (see FIG. 19) is remarkably lowered and hence, there is a concern that an environment for inspection or treatment of an affected part cannot be accurately reproduced.

Accordingly, a tubular organ is immersed in the electrified bath 6 in which physiological saline is stored so as to maintain moisture in the tubular organ.

Then, by adhering a return electrode to a suitable outer surface of the tubular organ and by supplying electricity to the return electrode, training of a manipulation in inspection and operation using an endoscope under an environment where an actual tubular organ is disposed can be performed.

However, a conventional return electrode is formed of a flat surface plate and hence, a contact state of the return electrode is unstable due to deflection of an outer surface of a tubular organ. Further, electricity is supplied to the tubular organ from one place where the return electrode is mounted and hence, an electricity supply state is also unstable. Further, the return electrode is adhered by an adhesive agent and hence, a state where the return electrode is mounted is unstable, and the return electrode can be used only one time.

Figure 18:
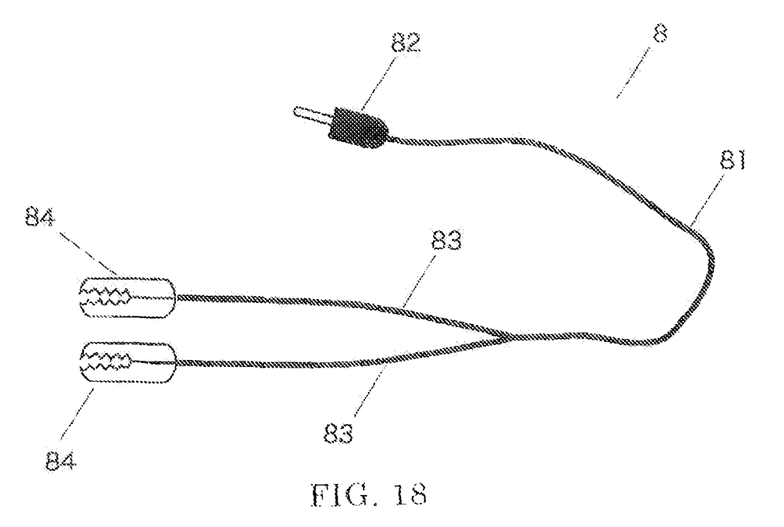
FIG. 18 is a plan view of an electricity supply cord according to the present invention.

In view of the above, in the present invention, as shown in FIG. 18, an electricity supply cord 8 is adopted where a connection plug 82 is connected to an end portion of a cord 81 on one side, the other side of the cord 81 is branched, and electricity supply clips 84, 84 are connected to end portions of respective branch cords 83, 83.

Figure 19:
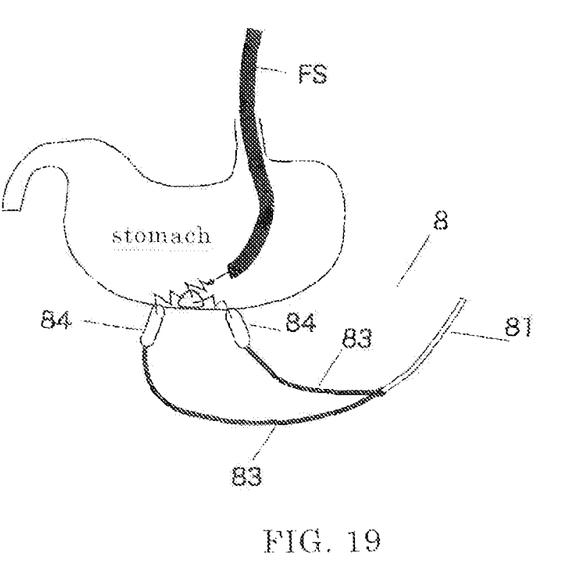
FIG. 19 is an explanatory view showing a method of removing by cutting a polyp generated on an inner wall of a stomach using the electricity supply cord.

With the use of such an electricity supply cord 8, as shown in FIG. 19, training of a manipulation of inspection and operation using an endoscope can be performed in a state where two portions of an outer wall surface around a polyp generated on an inner wall surface of a stomach which is a tubular organ are clamped by the electricity supply clips 84, 84.

In the above-mentioned configuration, an outer surface of a tubular organ is clamped by the electricity supply clips 84, 84 and hence, a stable contact state is acquired. Further, electricity is supplied from two portions which clamp the electricity supply clips 84, 84 clamp and hence, a stable electricity supply state can be also acquired. Further, with the use of the electricity supply clips 84, 84, a state where the electricity supply clips 84, 84 are mounted also becomes stable, and the electricity supply clips 84, 84 can be used any number of times.

In performing an endoscope manipulation training with a tubular organ such as a stomach ST cut away from a living body as a training object using the endoscope manipulation training apparatus 1 according to the present invention, the stomach ST is immersed in the electrified bath 6 in which physiological saline is stored so as to maintain moisture in the stomach ST.

Figure 21:
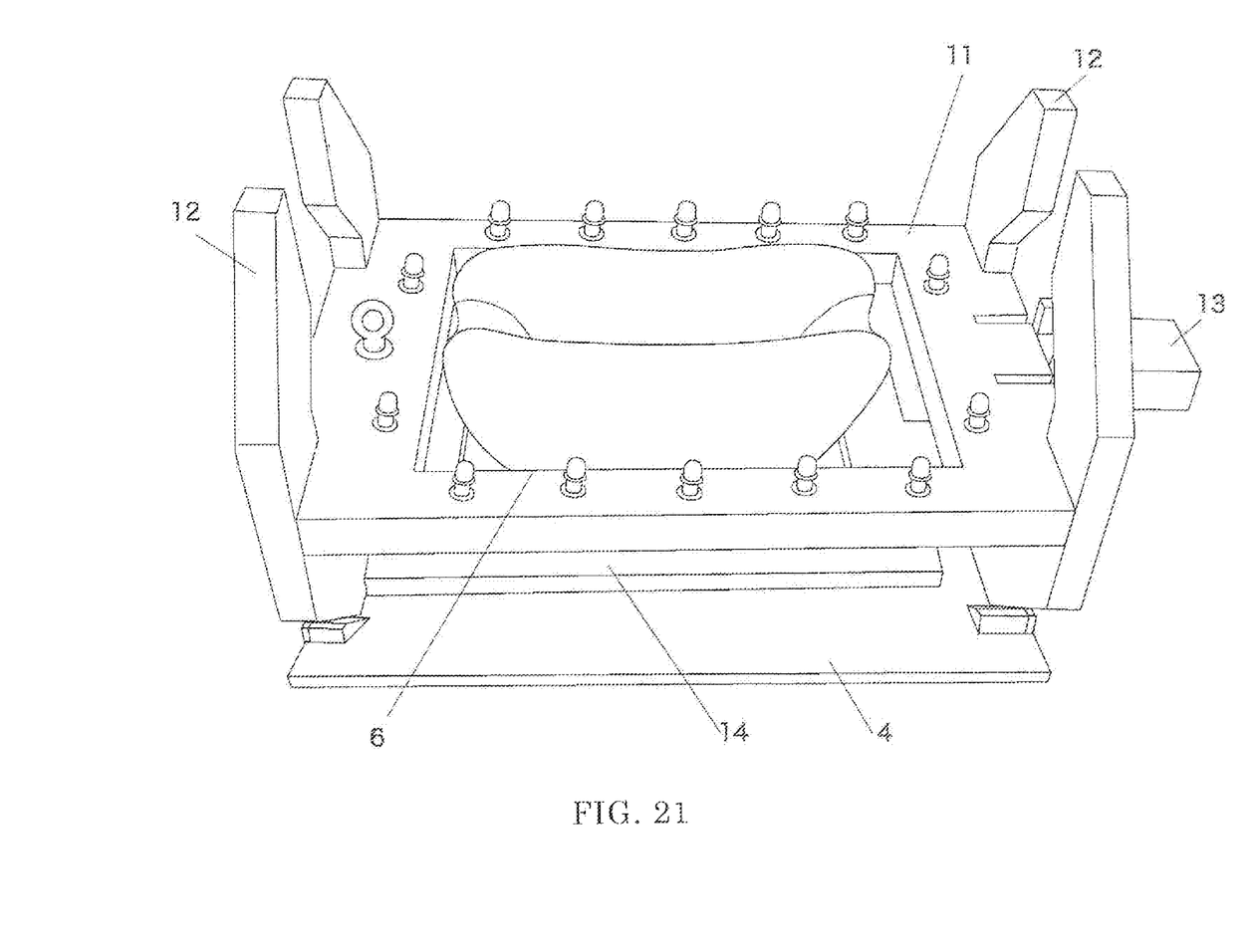
FIG. 21 is a perspective view showing a state where the electrified bath is mounted on the endoscope manipulation training apparatus.

Next, as shown in FIG. 21, in a state where the electrified bath support plate 14 is mounted on the body 2 of the endoscope manipulation training apparatus 1, the electrified bath 6 where physiological saline is stored and the stomach ST is immersed is mounted such that the electrified bath 6 is fitted in the opening portion 141 of the electrified bath support plate 14.

By arranging an insertion tube 5B shown in FIG. 16 in one side portion of the electrified bath 6 in which the stomach ST is immersed and by fitting a distal end portion 51a of a tubular portion 51 into an opening portion of the stomach ST at one end, training of an endoscope manipulation can be performed using the endoscope manipulation training apparatus 1.

In such an endoscope manipulation training apparatus 1, the electrified bath 6 is formed of a bag-shaped bath having flexibility. With respect to the front portion 62 and the back portion 63, a width of both end portions 62b, 63b is set slightly narrower than a width of the intermediate portions 62a, 63a and hence, the stomach ST can be surely held so that the stomach ST is not moved upward, downward, leftward, or rightward.

Figure 22:
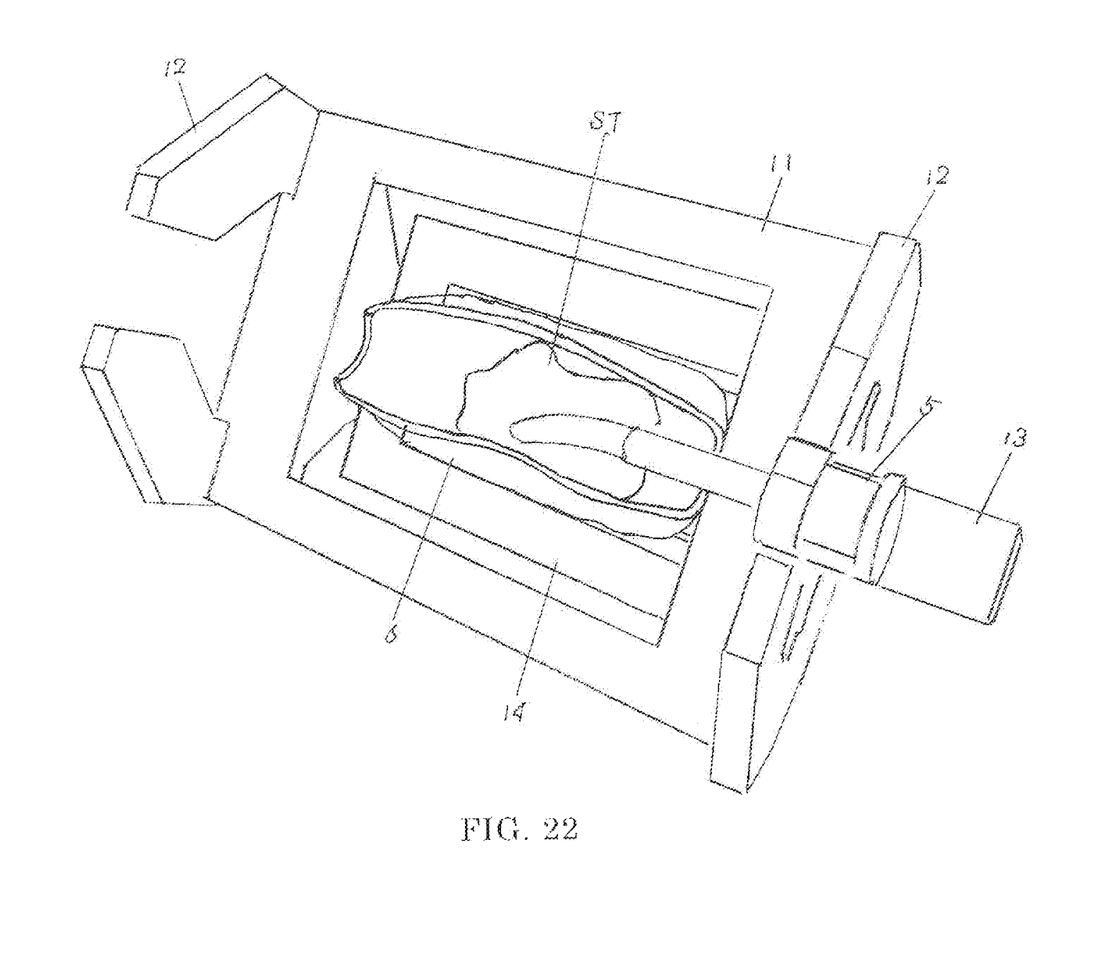
FIG. 22 is a perspective view showing a state where the endoscope manipulation training apparatus shown in FIG. 21 is rotated.

Accordingly, as shown in FIG. 22, even when training of an endoscope manipulation is performed by rotating the body 2 of the endoscope manipulation training apparatus 1 at a predetermined angle, training can be performed in a stable state.

As has been described heretofore, according to the endoscope manipulation training apparatus 1 of the present invention, assembling, disassembling and the like of the apparatus can be performed easily and hence, mounting and exchanging of an tubular organ do not take time, and cleaning or the like of the apparatus can be performed easily.

When endoscope manipulation training is performed, the apparatus is minimally rotated, and the electrified bath 6 in which physiological saline is stored is minimally moved thus providing excellent stability to the endoscope manipulation training apparatus.

It is claimed:

1. An endoscope manipulation training apparatus comprising: a body including an organ support plate, two support leg plates, and an insertion tube support body; and a synthetic-resin-made net body having flexibility, wherein an opening portion is formed in a center portion of the organ support plate, fitting portions are formed on both end portions of the organ support plate, threaded holes are formed in both corner portions of both end surfaces of the organ support plate, a fitting hole is formed in one of the fitting portions such that the fitting hole extends inward from an end surface of the fitting portion, and a latch groove is formed in the one of the fitting portions on both sides of the fitting hole, the two support leg plates are formed such that an outer peripheral surface and an inner peripheral surface exhibit a regular octagonal shape, cutaway portions are formed in the upper end portions of the support leg plates, fitting grooves are formed in center portions of the inner peripheral surface of the support leg plates, and insertion holes are formed in the support leg plates on outer sides with respect to the fitting grooves, and the insertion tube support body includes a protruding portion, a holding portion, and a fitting engagement groove, and the protruding portion is fitted into the fitting hole of the organ support plate.

2. The endoscope manipulation training apparatus according to claim 1, wherein the body further includes an electrified bath support plate, and an opening portion is formed in a center portion of the electrified bath support plate, and placing portions are formed on both end portions of the electrified bath support plate.

3. The endoscope manipulation training apparatus according to claim 1, further comprising a base, wherein the base includes a rectangular base plate, and pedestal bodies disposed on four corner portions of the base plate.

4. The endoscope manipulation training apparatus according to claim 2, further comprising a base, wherein the base includes a rectangular base plate, and pedestal bodies disposed on four corner portions of the base plate.

* * * * *